United States Patent [19]

Bell et al.

[11] Patent Number: 4,994,428

[45] Date of Patent: Feb. 19, 1991

[54] METHOD FOR PREPARING A PROMOTED IRON CATALYST AND CATALYST PREPARED BY THE METHOD FOR CONVERSION OF SYNTHESIS GAS TO LIQUID HYDROCARBONS

[75] Inventors: Weldon K. Bell, Pennington; Werner O. Haag, Lawrenceville, both of N.J.

[73] Assignee: Mobil Oil Corp., New York, N.Y.

[21] Appl. No.: 324,796

[22] Filed: Mar. 17, 1989

[51] Int. Cl.$^5$ .............................................. B01J 23/78
[52] U.S. Cl. .................................................... 502/330
[58] Field of Search ........................................ 502/330

[56] References Cited

U.S. PATENT DOCUMENTS

| | | | |
|---|---|---|---|
| 2,541,671 | 2/1951 | Segura et al. | 502/330 |
| 4,252,736 | 2/1981 | Haag et al. | 260/450 |
| 4,338,089 | 7/1982 | Schaper et al. | 518/707 |

OTHER PUBLICATIONS

L. König et al., "The Influence of Water and of Alkali Promoter on the Carbon Number Distribution, etc.", Ber. Bunsenges. Phys. Chem., 91, 116–121 (1987).

*Primary Examiner*—W. J. Shine
*Attorney, Agent, or Firm*—Alexander J. McKillop; Charles J. Speciale; Dennis P. Santini

[57] ABSTRACT

A novel Fischer Tropsch iron catalyst that has unusually high selectivity for liquid hydrocarbons (low selectivity for methane) is provided. The catalyst is prepared by treatment of the usual inactive catalyst precursor with water vapor at elevated temperature either after conventional activation by syngas or concurrently therewith. Surprisingly, the "selectivation" with water vapor does not affect catalytic activity. The novel "selectivated" catalyst may be used to advantage either to increase temperature and throughput, or to increase liquid hydrocarbon selectivity, compared with conventional catalyst that has not been "selectivated".

18 Claims, 5 Drawing Sheets

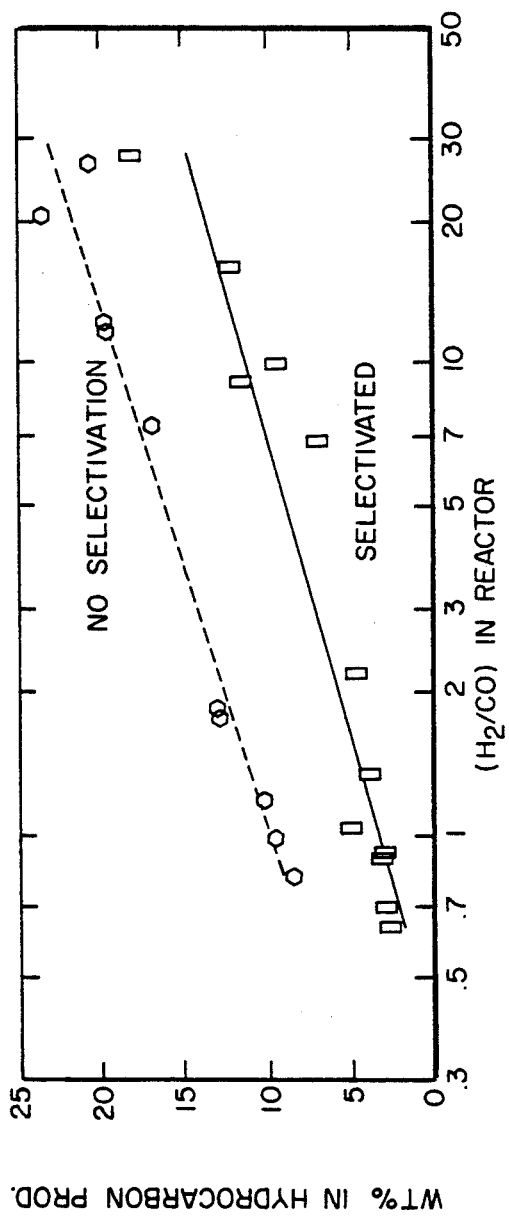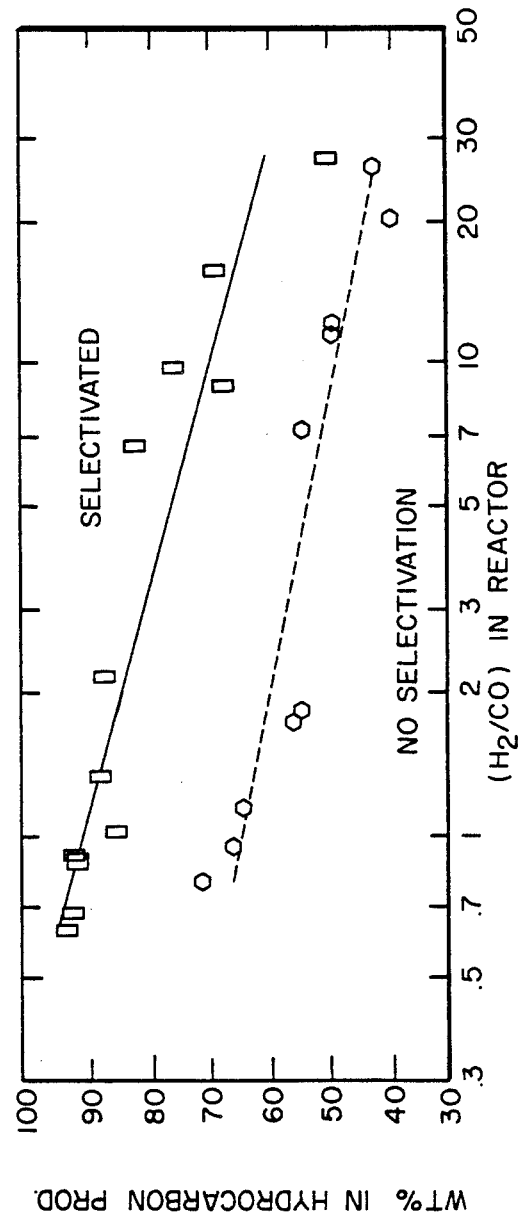
FIG. 2A
FIG. 2B

METHOD FOR PREPARING A PROMOTED IRON CATALYST AND CATALYST PREPARED BY THE METHOD FOR CONVERSION OF SYNTHESIS GAS TO LIQUID HYDROCARBONS

FIELD OF THE INVENTION

This invention is concerned with the conversion of synthesis gas, i.e. mixtures of gaseous carbon oxide with hydrogen or hydrogen donors, to hydrocarbon mixtures. In particular, it is concerned with improving the selectivity of a Fischer Tropsch iron catalyst whereby increased yield of liquid hydrocarbons are obtained.

BACKGROUND OF THE INVENTION

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture is given in Encyclopedia of Chemical Technology, Edited by Kirk-Othmer, Second Edition, Volume 10, pages 353–433, (1966), Interscience Publishers, New York, N.Y., the contents of which are herein incorporated by reference for background. The techniques for gasification of coal or other solid, liquid or gaseous fuel are not per se considered part of the present invention.

It is known that synthesis gas can be converted to reduction products of carbon monoxide, such as hydrocarbons, at from about 150° C. to about 450° C., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides. The wide range of catalysts and catalyst modifications disclosed in the art and an equally wide range of conversion conditions for the reduction of carbon monoxide by hydrogen provide some flexibility toward obtaining selected types of products, and some control over their molecular weight distribution. Ruthenium catalyst, for example, is capable of producing linear hydrocarbons exclusively, while "promoted iron" also produces oxygenates. Nonetheless, these conversions still leave much to be desired because either the catalyst is costly or by-products are produced in excessive amount. A review of the status of this art is given in "Carbon Monoxide-Hydrogen Reactions", Encyclopedia of Chemical Technology, Edited by Kirk-Othmer, Second Edition, Volume 4, pp. 446–488, Interscience Publishers, New York, N.Y., the text of which is incorporated herein by reference for background.

The molecular weight distribution of the product in the Fischer Tropsch reaction is controlled to a great extent by the nature of the reaction, and it is generally recognized that the steady state products of the reaction follow the Schulz-Flory distribution. See, e.g., P. Biloen and W. M. H. Sachtler, *Advance-in Catalysis*, Vol. 30, pp. 169–171 (Academic Press, New York, N.Y., 1981), which is herein incorporated by reference for background. Very briefly, for this is well described elsewhere, if the synthesis that takes place is characterized by a stepwise if the synthesis that takes place is characterized by a stepwise addition of a single carbon species to a growing hydrocarbon chain with a propagation rate constant $k_p$, and if this step competes with a growth-terminating step having the rate constant $k_t$, then the chances for any intermediate species to propagate rather than terminate is described by $\alpha$, wherein $$\alpha = k_p/(k_p + k_t)$$

If $\alpha$ is independent of the molecular weight of the intermediate, $$\log C_n = Constant + n(\log \alpha)$$

where $C_n$ is the mole percent of the (n)th-mer in the product and n is the number of carbon atoms contained in that species. A plot of $\log C_n$ vs n provides a straight line with the slope $\log \alpha$.

The significance of the foregoing relationship for producing hydrocarbons by the Fischer Tropsch process is that a reduction of by-product methane formation also reduces larger amounts of $C_2$, $C_3$, and $C_4$ hydrocarbons and causes a significant increase in the total yield of $C_5+$ liquids, with more liquid in the diesel fuel range being formed.

In brief, when practitioners in the Fischer Tropsch art refer to the selectivity of a catalyst or process in terms of the relative amount of methane that is produced, it is generally understood in the context of the overall changes in the distribution of normally gaseous and liquid hydrocarbon product as outlined above. It is generally recognized in this art, however, that selectivity is a function not only of the catalyst composition and its method of preparation, but also is a function of process conditions, particularly temperature, and a function of synthesis gas composition. In general, a decrease in temperature results in improved selectivity for liquid hydrocarbons, and a similar result tends to be achieved with a synthesis gas that, within limits, is relatively rich in carbon monoxide. In principle, of course, selectivity for increased liquid hydrocarbons can be obtained by simply lowering temperature, but such an expedient also lowers conversion. As a practical matter, therefore, there is a lower temperature limit, dictated by the economically required conversion rate below which operation becomes impractical.

Precipitated iron catalysts have been extensively studied and have been used for many years in the Fischer-Tropsch liquid phase process for synthesis of hydrocarbons. In general, they are inexpensive, exhibit good activity, and have adequate useful life. They almost always contain potassium promoter, which serves to reduce the amount of methane and other light hydrocarbon by-products. However, the amount of potassium that is normally used is limited to about 0.6 wt%, since larger amounts do not appear to offer further benefit with regard to methane reduction, and in fact increase the production of oxygenated by-products. Thus, there is a need for an iron catalyst having a higher selectivity for liquid hydrocarbons than is presently achieved in order to increase the total liquid hydrocarbons formed, especially those in the boiling range of high quality diesel fuel.

Conventional techniques for the production of a precipitated, inactive iron catalyst in large quantity and its activation prior to use are described by H. Koelbel and M. Ralek, Catalysis Review-Sci. Eng. (1980) Volume 21, pp. 242-249, the entire content of which is incorporated herein by reference as if fully set forth. The initial steps in the preparation of the precipitated inorganic iron catalyst useful in this invention are conventional. Ferric nitrate, which may be obtained by dissolving wrought iron scrap or steel turnings in nitric acid or, alternatively, from another source, is dissolved in water. The solution should be adjusted, if necessary, so that it contains a predetermined small amount of copper. The iron is then precipitated with ammonia or ammonium carbonate. Potassium carbonate is then added to the filtered and washed precipitate to provide a content of 0.1 to about 1.0 wt% potassium carbonate based on iron. The preferred potassium carbonate level is about 0.2 to 0.6 wt% based on iron content.

The filter cake produced by the technique just described and followed by the conventional step of calcining in air at e.g. 572° F., usually contains well in excess of 1000 ppm (parts per million) of nitrogen. For certain special applications, an iron catalyst having a nitrogen content less than 200 ppm, preferably less than 100 ppm, may be needed. Such catalyst may be prepared by bringing together the ammonia solution and the ferric nitrate solution at controlled rates such that the pH of the cooled supernatant liquid containing the precipitated catalyst is maintained at about 6.8. The filter cake produced by this method is then washed with hot water until relatively free of nitrate ion. The resulting calcined filter cake produced by this technique is of low nitrogen content. For further details, see U.S. Pat. No. 4,617,288 to Bell et al., incorporated herein by reference.

It is generally known that iron catalysts, as initially formed, are inactive in the Fischer Tropsch synthesis. They must be subjected to an activation step which comprises contacting the inactive solid with a reducing gas, such as synthesis gas, at elevated temperature.

During activation, the iron is partially reduced to the metallic bonding state. This activation is normally conducted in the absence of water.

Water is known to be a powerful inhibitor in the Fischer Tropsch synthesis. Carbon dioxide is also an inhibitor, but very much weaker than water. The primary step in the conversion produces water by reaction (I):

but much of the water is consumed by the shift reaction (II) catalyzed by the iron catalyst:

To minimize the inhibiting effect of water, the synthesis gas feed to the Fischer Tropsch process and the recycle streams usually are dried prior to contact with the iron catalyst.

It is an object of this invention to provide an iron catalyst having an unusually low selectivity for methane by-product. It is a further object of this invention to provide a precipitated iron catalyst which has a stable, unusually high selectivity for producing liquid hydrocarbons including substantial increments of diesel fuel. It is a further object of this invention to provide an improved liquid phase Fischer Tropsch process for synthesis of hydrocarbons which utilizes the novel selectivated activated iron catalyst produced by the method of this invention. These and other objects of this invention will become evident on reading this entire specification including the appended claims.

SUMMARY OF THE INVENTION

We have now found that the selectivity of a Fischer Tropsch iron catalyst is improved if the catalyst is subjected to a high partial pressure of water vapor at elevated temperature for a short period of time, either during or after the activation step, but before the catalyst is integrated into the production stream, all as more fully described hereinbelow. Since the principal effect of the treatment with water is to improve the selectivity of virgin catalyst with no substantial change of activity, we shall refer to this treatment as "selectivation" to distinguish it from "activation", the principal effect of which is to impart catalytic activity.

BRIEF DESCRIPTION OF THE DRAWINGS

FIGS. 2A and 2B respectively show methane and liquid hydrocarbon ($C_{5+}$) selectivity as a function of feed composition for Example 2.

EXAMPLES

Figure 1A:
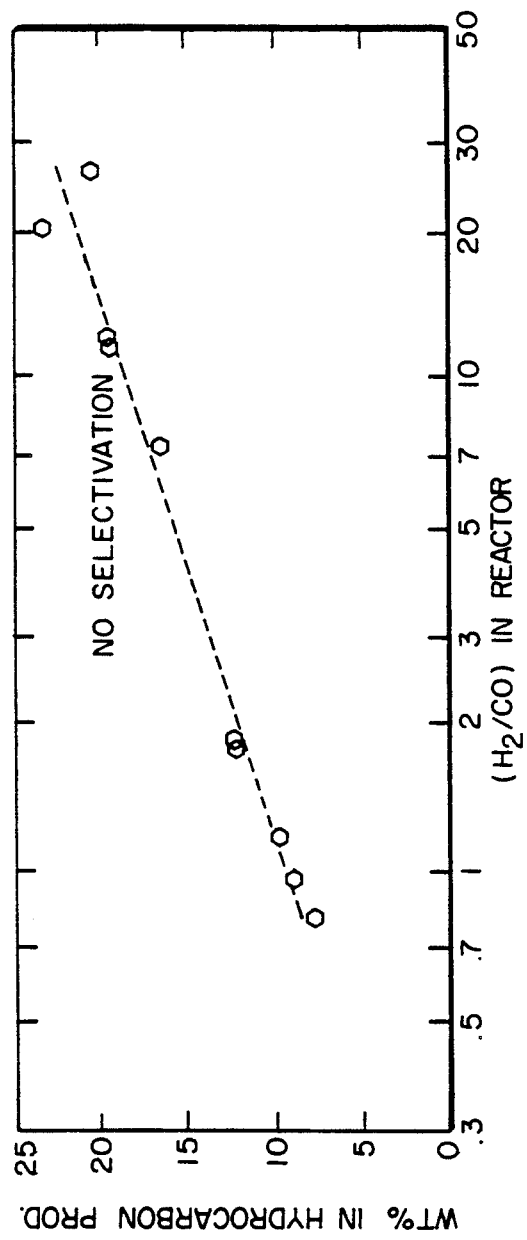
FIGS. 1A and 1B respectively show methane and liquid hydrocarbon ($C_{5+}$) selectivity as a function of feed composition for Example 1B.

It is believed that this invention will be understood best by examining the examples prior to the detailed description which follow the examples. The examples, however, are not to be construed as limiting the scope of the invention, which scope is determined by this entire specification including appended claims. All selectivities given herein are by weight percent; all catalyst composition are by weight; all ratios are molar ratios; and all syngas conversions are mole percent unless explicitly stated to be otherwise.

In the examples which follow, all of the selectivity values and other kinetic data were obtained by charging finely ground (inactive) iron catalyst (providing about 5 grams of Fe) to a continuous stirred tank reactor (CSTR) of 300 ml capacity that contained 120 to 200 cc hydrogenated decene trimer in which the catalyst is suspended (slurry reactor). The catalyst was then activated and selectivated as described in the specific examples.

After activation, catalyst behavior was determined by isothermal synthesis mostly conducted at about 265° C., with specific exceptions as shown in Tables I-V, and at about 235 psi and with high (1.9) and low (0.6) $H_2/CO$ ratio syngas feeds at various feed rates. With the CSTR system, it was possible, using these feeds, to vary the $H_2/CO$ ratio in the reactor over a wide range (from 0.6 to 30) by the simple expedient of varying the syngas feed rate.

FT catalyst selectivity was assessed by correlation with $H_2/CO$ ratio during reaction. This ratio is directly measured as that exiting from the CSTR. Selectivity was correlated with the $H_2/CO$ ratio as shown in FIG. 2. This technique allows selectivity comparisons that are independent of conversion. The left portion of the illustration is behavior typical of low $H_2/CO$ feeds as from advanced coal gasifiers, while the right portion is typical of $H_2$-rich feeds as from methane reformers.

EXAMPLE 1A

This example illustrates the preparation of a precipitated iron catalyst. Example 1B which follows illustrates conventional activation. Neither Example 1A nor 1B are considered part of the present invention, and are given only to provide selectivity and other data for comparison purposes.

Catalyst preparation was as follows. A stirred flask warmed with a heating mantle and equipped with a reflux condenser to minimize $NH_3$ loss was used. A 1360 gram portion of a 10 wt% $NH_3$ solution was quickly poured into a hot (102° C.) 1640-ml aqueous solution of 808 grams $Fe(NO_3)_3.9H_2O$ and 1.28 grams $Cu(NO_3)_2.3.1 H_2O$ with stirring; rapid precipitation resulted. The mixture pH varied from 6.9 just after base addition to 6.5 after the slurry temperature had returned to about 96° C. (approximately 5 minutes); digesting continued for another 18 minutes. The slurry was filtered in two equal portions. Each filter cake was washed with about 3.5 liters of hot (90°-100° C.) water in 17½ 200 ml portions. A 30 gram portion of the filter cake was reserved leaving a 1048 gram portion containing an estimated 107 gram Fe. This large portion was slurried with an added 1.4 liters water and then a 1025 ml of solution containing 0.615 gram $K_2CO_3$ was slowly added. The slurry was then filtered (but not washed), dried overnight in the filter at room conditions, dried in air at 120° C. for 17 hours, and calcined at 320° C. for 6 hours. Assay indicated that $Fe/Cu/K_2CO_3$ was 100/0.2/0.4 parts by weight. It should be understood that although potassium content is expressed as $K_2CO_3$, the potassium can be introduced and be present in other form (e.g. $K_2O$, $K_2OAc$, KOH, etc.).

EXAMPLE 1B

In this example a portion of the inactive iron catalyst prepared in Example 1A was charged to the slurry CSTR reactor described above and activated, in conventional manner, by passing through the reactor 6 NL/GFe/HR (Normal liters, i.e. liters of $H_2+CO$, at 273° K. and 1 atmosphere per gram of iron per hour) of dry syngas having a $H_2/CO$ ratio of about 0.7 for 3 to 5 hours at a pressure of 35 psi, while maintaining the reactor temperature at 280°-290° C.

After activation, the temperature was dropped and maintained at about 265°-266° C. and the pressure increased while continuing to feed syngas. The data obtained for different syngas compositions and at different space velocities are summarized in Table I.

Figure 1B:
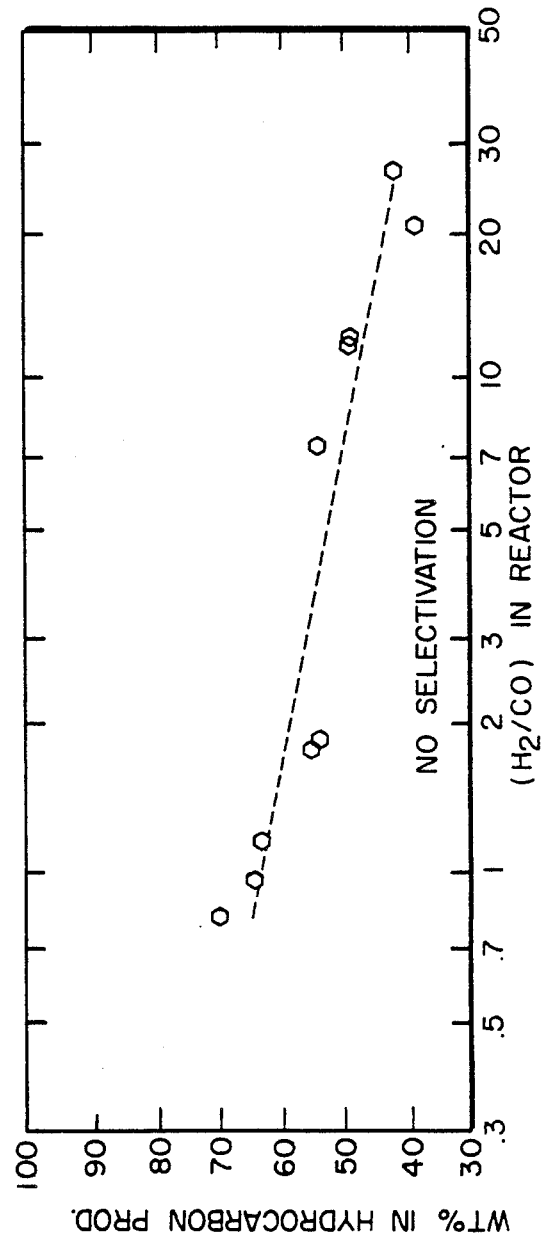

The methane selectivity of the catalyst and the selectivity for liquid hydrocarbons as a function of feed composition are shown in FIGS. 1A and 1B, respectively.

TABLE I (EXAMPLE 1B) PRIOR ART CATALYST PERFORMANCE

| | RUN BALANCE | | | | |
|---|---|---|---|---|---|
| | A | B | C | D | E |
| HOURS ON STREAM | 19.25 | 21.00 | 24.68 | 43.52 | 46.50 |
| TEMPERATURE °C. | 266.00 | 266.00 | 266.00 | 266.00 | 266.00 |
| PRESSURE PSIG | 202.00 | 202.00 | 202.00 | 202.00 | 202.00 |
| SV NL/GFE/HR | 1.27 | 3.54 | 2.52 | 0.64 | 3.70 |
| FEED [$H_2/CO$] | 0.72 | 0.72 | 0.72 | 0.72 | 0.72 |
| SYNGAS CONV % | 90.44 | 72.87 | 81.29 | 91.92 | 59.69 |
| $H_2$ CONV % | 85.36 | 68.23 | 75.97 | 87.42 | 56.90 |
| CO CONV % | 94.10 | 76.22 | 85.12 | 95.17 | 61.71 |
| HYDROCARBON SELECTIVITIES, WT % OF HC | | | | | |
| CH4 | 12.26 | 9.00 | 9.76 | 12.42 | 7.74 |
| $C_2H_6$ | 8.74 | 5.74 | 6.42 | 8.92 | 3.59 |
| $C_2H_4$ | 0.69 | 1.96 | 1.32 | 0.63 | 2.73 |
| $C_3H_8$ | 7.48 | 3.00 | 3.59 | 8.29 | 1.69 |
| $C_3H_6$ | 6.91 | 8.90 | 8.53 | 6.66 | 8.28 |
| $C_4H_{10}$ | 3.86 | 2.22 | 2.43 | 3.90 | 1.60 |
| $C_4H_8$ | 5.81 | 5.78 | 5.65 | 5.85 | 5.59 |
| $C_5+$ | 54.25 | 63.41 | 62.31 | 53.32 | 68.80 |
| EXIT [$H_2/CO$] | 1.79 | 0.96 | 1.16 | 1.88 | 0.81 |
| [$H_2 + CO_2/H_2O + CO$] | 39.00 | 11.73 | 20.64 | 56.19 | 9.59 |
| | RUN BALANCE | | | | |
| | F | G | H | I | J |
| HOURS ON STREAM | 66.72 | 70.83 | 72.67 | 91.53 | 95.33 |
| TEMPERATURE °C. | 265.00 | 265.00 | 265.00 | 265.00 | 265.00 |
| PRESSURE PSIG | 202.00 | 202.00 | 202.00 | 202.00 | 202.00 |
| SV NL/GFE/HR | 0.61 | 3.64 | 2.48 | 0.31 | 1.26 |
| FEED [$H_2/CO$] | 1.87 | 1.87 | 1.87 | 1.87 | 1.87 |
| SYNGAS CONV % | 64.12 | 51.52 | 56.81 | 68.87 | 57.54 |
| $H_2$ CONV % | 47.52 | 34.52 | 38.97 | 53.99 | 39.87 |
| CO CONV % | 95.21 | 83.35 | 90.24 | 96.73 | 90.65 |
| HYDROCARBON SELECTIVITIES, WT % OF HC | | | | | |
| CH4 | 23.07 | 16.45 | 19.21 | 20.14 | 19.32 |
| $C_2H_6$ | 10.74 | 6.05 | 7.58 | 10.14 | 7.61 |
| $C_2H_4$ | 1.25 | 1.74 | 1.38 | 1.50 | 1.29 |
| $C_3H_8$ | 7.44 | 3.77 | 4.86 | 6.51 | 4.75 |
| $C_3H_6$ | 9.33 | 9.10 | 9.17 | 10.37 | 9.19 |
| $C_4H_{10}$ | 4.39 | 3.30 | 3.64 | 4.07 | 3.69 |
| $C_4H_8$ | 5.87 | 6.21 | 6.08 | 6.38 | 6.01 |

TABLE I-continued

(EXAMPLE 1B)
PRIOR ART CATALYST PERFORMANCE

| | | | | | |
|---|---|---|---|---|---|
| $C_5+$ | 37.91 | 53.37 | 48.09 | 40.88 | 48.15 |
| EXIT [$H_2$/CO] | 20.52 | 7.36 | 11.72 | 26.32 | 12.04 |
| [$H_2 + CO_2$/$H_2O$ + CO] | 48.53 | 30.72 | 34.96 | 44.59 | 42.89 |

EXAMPLE 2

In this example a portion of the inactive iron catalyst from example 1A was activated in the conventional manner in the back-mixed reactor by the procedure described in Example 1B. After activation, the catalyst was selectivated by contact at 261° C. for 32 hours with a stream of $N_2$ gas and water vapor at about 17 atmospheres total pressure. The water was fed at 0.44 g/$g_{Fe}$/hr, providing a partial pressure of 5 atmospheres of steam in the reactor.

Following activation, the temperature was maintained at about 265°-266° C. while syngas was fed as in Example 1B. The data obtained for different syngas compositions and at different space velocities are summarized in Table II. FIGS. 2A and 2B illustrates the marked increase in selectivity compared with Example 1B over a wide range of conditions. As is evident from Table II, no loss of activity results from selectivation (e.g. compare Table I-H with Table II-D).

EXAMPLE 3

This example illustrates that effective selectivation is achieved when conventional catalyst activation is conducted in the presence of sufficiently high vapor pressure of water, i.e. when activation and selectivation are done concurrently.

A portion of the catalyts of Example 1A was loaded into the slurry reactor as described in Example 1B. The catalyst was then treated for 3.8 hours at 280°-290° C. and a total pressure of 35 psig with a wet syngas having a molar ratio of $H_2$/CO=1.9 and a ratio of $$H_2O/[H_2+CO]=0.1$$

while maintaining the flow rate of the syngas (dry basis) at 6 Nl/$g_{Fe}$/hr.

The temperature was then dropped, the pressure increased, and dry syngas fed, as in Example 1B. The results are shown in Table III. Selectivation effective-

TABLE II

(EXAMPLE 2)

| | RUN BALANCE | | | | | |
|---|---|---|---|---|---|---|
| | A | B | C | D | E | F |
| HOURS ON STREAM | 94.83 | 99.92 | 118.75 | 125.58 | 142.83 | 148.33 |
| TEMPERATURE °C. | 266.00 | 265.00 | 266.00 | 265.00 | 266.00 | 266.00 |
| PRESSURE PSIG | 230.00 | 230.00 | 230.00 | 230.00 | 230.00 | 230.00 |
| SV NL/GFE/HR | 1.25 | 2.40 | 0.68 | 2.45 | 0.31 | 1.25 |
| FEED [$H_2$/CO] | 0.63 | 0.63 | 0.63 | 1.92 | 1.92 | 1.92 |
| SYNGAS CONV % | 68.73 | 67.35 | 86.76 | 55.49 | 64.18 | 51.48 |
| $H_2$ CONV % | 61.24 | 60.27 | 80.38 | 39.08 | 47.47 | 33.07 |
| CO CONV % | 73.46 | 71.81 | 90.78 | 87.05 | 96.31 | 86.91 |
| HYDROCARBON SELECTIVITIES, WT % OF HC | | | | | | |
| $CH_4$ | 2.34 | 2.43 | 3.35 | 10.97 | 17.52 | 9.02 |
| $C_2H_6$ | 0.55 | 0.50 | 1.17 | 4.35 | 8.33 | 2.52 |
| $C_2H_4$ | 1.55 | 1.63 | 1.79 | 2.64 | 2.79 | 2.84 |
| $C_3H_8$ | 0.37 | 0.43 | 0.64 | 2.25 | 4.37 | 1.86 |
| $C_3H_6$ | 2.38 | 2.46 | 3.41 | 7.17 | 9.58 | 4.85 |
| $C_4H_{10}$ | 0.36 | 0.42 | 0.58 | 1.94 | 2.94 | 1.63 |
| $C_4H_8$ | 1.84 | 1.92 | 2.74 | 5.33 | 5.44 | 3.86 |
| $C_5+$ | 90.62 | 90.21 | 86.32 | 65.34 | 49.01 | 73.41 |
| EXIT [$H_2$/CO] | 0.92 | 0.89 | 1.34 | 9.05 | 27.39 | 9.84 |
| [$H_2 + CO_2$/$H_2O$ + CO] | 16.96 | 18.11 | 38.81 | 34.12 | 56.92 | 36.77 |

Figure 3A:
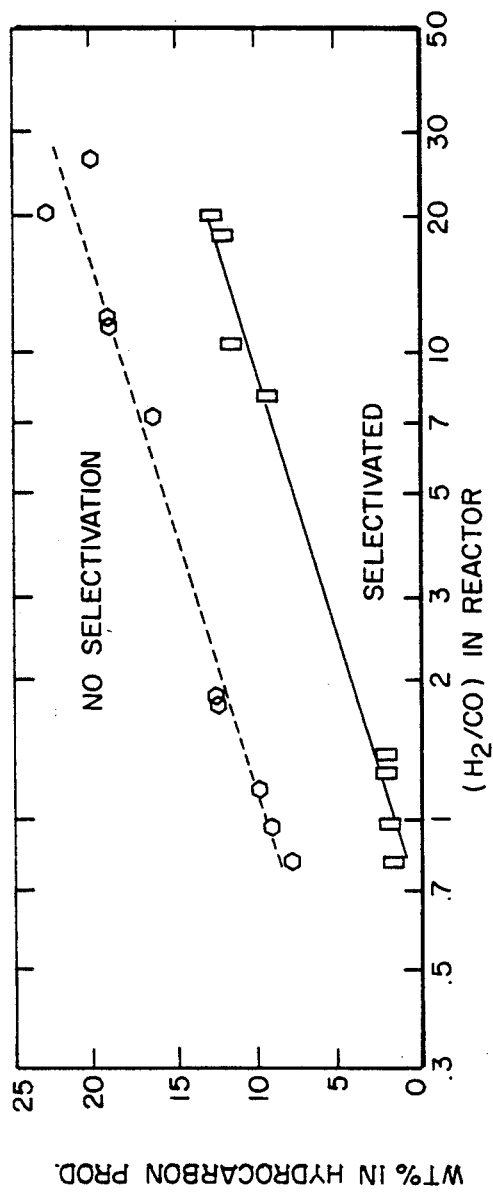
FIGS. 3A and 3B respectively show methane and liquid hydrocarbon ($C_{5+}$) selectivity as a function of feed composition for Example 3.
Figure 3B:
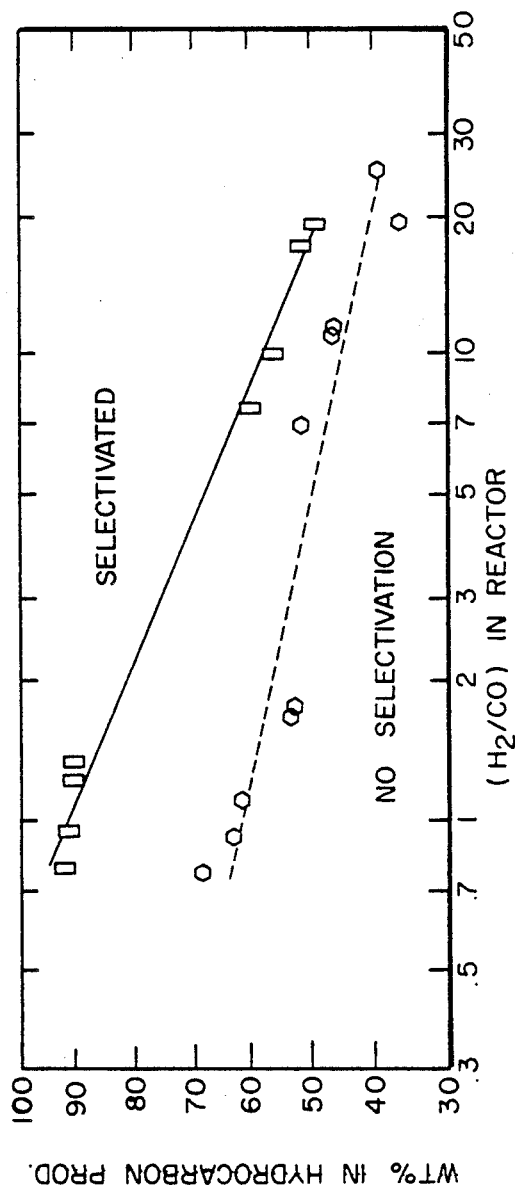

| | RUN BALANCE | | | | | |
|---|---|---|---|---|---|---|
| | G | H | I | J | K | L |
| HOURS ON STREAM | 166.33 | 190.83 | 222.88 | 251.22 | 262.50 | 269.92 |
| TEMPERATURE °C. | 265.00 | 222.00 | 219.00 | 219.50 | 262.00 | 219.00 |
| PRESSURE PSIG | 230.00 | 230.00 | 235.00 | 240.00 | 240.00 | 240.00 |
| SV NL/GFE/HR | 0.63 | 0.29 | 0.28 | 0.53 | 0.53 | 1.19 |
| FEED [$H_2$/CO] | 1.92 | 1.92 | 0.63 | 0.63 | 0.63 | 1.92 |
| SYNGAS CONV % | 57.81 | 46.12 | 48.61 | 25.24 | 84.52 | 12.74 |
| $H_2$ CONV % | 39.70 | 28.63 | 45.94 | 25.17 | 79.69 | 9.03 |
| CO CONV % | 92.64 | 79.77 | 50.29 | 25.28 | 87.57 | 19.87 |
| HYDROCARBON SELECTIVITIES, WT % OF HC | | | | | | |
| $CH_4$ | 11.69 | 6.49 | 2.22 | 2.13 | 4.39 | 4.10 |
| $C_2H_6$ | 3.40 | 1.80 | 0.49 | 0.61 | 1.28 | 0.00 |
| $C_2H_4$ | 3.32 | 2.17 | 1.33 | 1.18 | 2.21 | 3.12 |
| $C_3H_8$ | 2.35 | 1.70 | 0.66 | 0.62 | 0.88 | 1.22 |
| $C_3H_6$ | 5.91 | 3.36 | 1.92 | 1.81 | 3.87 | 2.77 |
| $C_4H_{10}$ | 1.90 | 1.68 | 0.76 | 0.69 | 0.82 | 1.31 |
| $C_4H_8$ | 4.53 | 2.70 | 1.63 | 1.47 | 2.98 | 1.73 |
| $C_5+$ | 66.91 | 80.10 | 90.98 | 91.50 | 83.56 | 85.75 |
| EXIT [$H_2$/CO] | 15.77 | 6.79 | 0.69 | 0.63 | 1.03 | 2.18 |
| [$H_2 + CO_2$/$H_2O$ + CO] | 41.69 | 42.34 | 8.54 | 5.22 | 26.14 | 5.39 | ness by combined treatment is evident. Methane and liquid hydrocarbon selectivities are shown in FIGS. 3A and 3B, respectively.

Figure 4A:
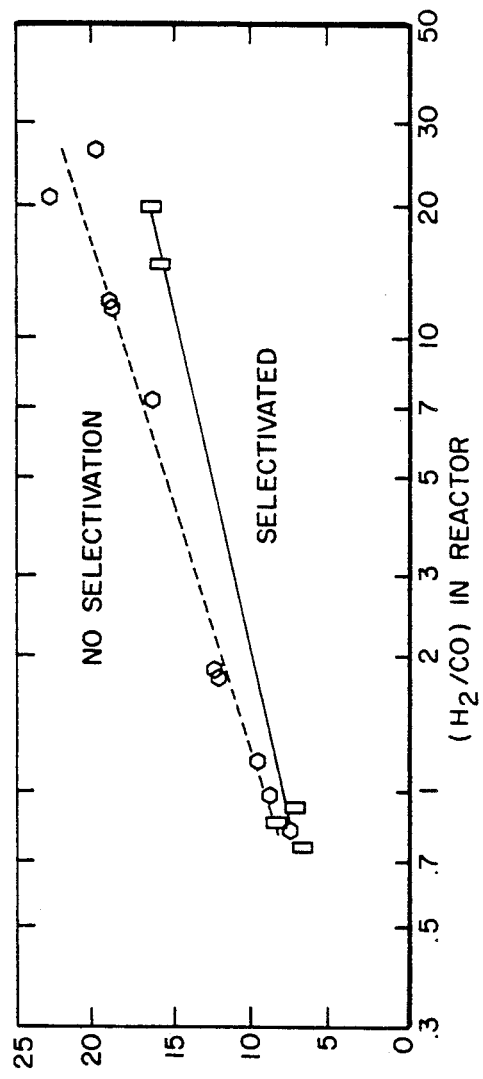
FIGS. 4A and 4B respectively show methane and liquid hydrocarbon ($C_{5+}$) selectivity as a function of feed composition for Example 4.
Figure 4B:
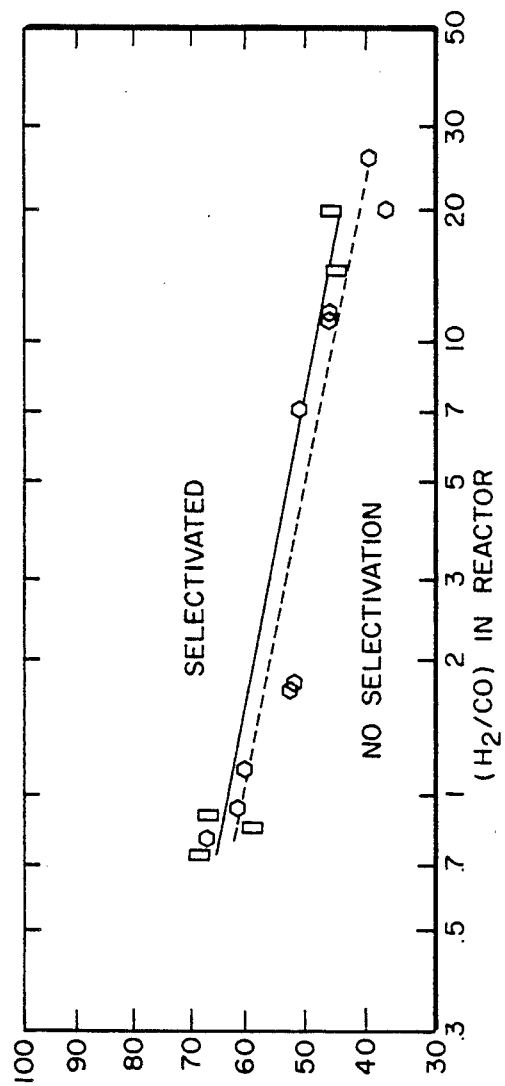

FIG. 4. As can be seen from FIGS. 4A and 4B, the selectivation was sharply less effective than in Example 3, even though a longer treatment time was used.

TABLE III (EXAMPLE 3)
COMBINED SELECTIVATION - ACTIVATION

| | RUN BALANCE | | | | | | | |
|---|---|---|---|---|---|---|---|---|
| | A | B | C | D | E | F | G | H |
| HOURS ON STREAM | 22.33 | 27.53 | 46.42 | 50.75 | 53.42 | 70.42 | 76.92 | 94.83 |
| TEMPERATURE °C. | 267.00 | 267.00 | 266.00 | 266.00 | 265.00 | 261.00 | 266.00 | 266.00 |
| PRESSURE PSIG | 235.00 | 235.00 | 230.00 | 230.00 | 230.00 | 230.00 | 230.00 | 235.00 |
| SV NL/GFE/HR | 1.28 | 2.36 | 1.27 | 3.30 | 3.44 | 1.32 | 2.49 | 1.34 |
| FEED [$H_2$/CO] | 1.92 | 1.92 | 1.92 | 1.92 | 0.60 | 0.60 | 0.60 | 0.60 |
| SYNGAS CONV % | 66.58 | 58.68 | 64.59 | 55.25 | 77.64 | 89.28 | 84.80 | 89.73 |
| $H_2$ CONV % | 51.64 | 42.64 | 49.01 | 39.41 | 73.08 | 83.28 | 79.87 | 84.63 |
| CO CONV % | 95.34 | 89.55 | 94.57 | 85.73 | 80.39 | 92.89 | 87.77 | 92.80 |
| HYDROCARBON SELECTIVITIES, WT % OF HC | | | | | | | | |
| $CH_4$ | 12.66 | 11.53 | 11.95 | 9.36 | 1.40 | 1.94 | 1.68 | 1.95 |
| $C_2H_6$ | 7.23 | 5.90 | 6.50 | 4.31 | 0.30 | 0.68 | 0.46 | 0.73 |
| $C_2H_4$ | 2.12 | 1.92 | 2.06 | 2.29 | 1.24 | 1.34 | 1.20 | 1.23 |
| $C_3H_8$ | 4.39 | 3.57 | 3.91 | 2.64 | 0.29 | 0.32 | 0.26 | 0.33 |
| $C_3H_6$ | 11.31 | 9.53 | 10.63 | 9.00 | 1.97 | 2.48 | 1.99 | 2.44 |
| $C_4H_{10}$ | 3.49 | 3.37 | 3.20 | 2.73 | 0.66 | 0.32 | 0.97 | 0.34 |
| $C_4H_8$ | 7.01 | 6.11 | 8.10 | 7.52 | 1.85 | 2.02 | 1.72 | 2.11 |
| $C_5+$ | 51.79 | 58.05 | 53.64 | 62.14 | 92.30 | 90.90 | 91.71 | 90.87 |
| EXIT [$H_2$/CO] | 19.98 | 10.56 | 18.07 | 8.17 | 0.83 | 1.41 | 0.99 | 1.28 |
| [$H_2 + CO_2/H_2O + CO$] | 33.40 | 23.70 | 33.51 | 21.04 | 13.73 | 30.49 | 22.29 | 35.18 |

TABLE IV (EXAMPLE 4)

| | RUN BALANCE | | | | |
|---|---|---|---|---|---|
| | A | B | C | D | E |
| HOURS ON STREAM | 24.08 | 29.50 | 48.67 | 55.08 | 72.33 |
| TEMPERATURE °C. | 266.00 | 266.00 | 266.00 | 266.00 | 266.00 |
| PRESSURE PSIG | 230.00 | 230.00 | 230.00 | 230.00 | 230.00 |
| SV NL/GFE/HR | 1.39 | 2.54 | 0.73 | 2.41 | 1.27 |
| FEED [$H_2$/CO] | 0.60 | 0.60 | 0.60 | 1.92 | 1.92 |
| SYNGAS CONV % | 92.22 | 85.40 | 95.80 | 64.21 | 65.83 |
| $H_2$ CONV % | 90.04 | 83.27 | 94.81 | 49.04 | 50.53 |
| CO CONV % | 93.53 | 86.68 | 96.40 | 93.40 | 95.25 |
| HYDROCARBON SELECTIVITIES, WT % OF HC | | | | | |
| $CH_4$ | 7.60 | 6.91 | 8.61 | 16.02 | 16.54 |
| $C_2H_6$ | 4.53 | 3.75 | 6.28 | 8.60 | 8.18 |
| $C_2H_4$ | 1.07 | 1.51 | 0.90 | 1.51 | 1.67 |
| $C_3H_8$ | 2.49 | 1.87 | 4.64 | 5.64 | 5.31 |
| $C_3H_6$ | 7.69 | 7.57 | 9.36 | 9.94 | 10.31 |
| $C_4H_{10}$ | 1.83 | 1.79 | 2.72 | 3.84 | 3.88 |
| $C_4H_8$ | 6.14 | 6.51 | 7.07 | 7.90 | 6.45 |
| $C_5+$ | 68.66 | 70.09 | 60.42 | 46.55 | 47.66 |
| EXIT [$H_2$/CO] | 0.93 | 0.76 | 0.87 | 14.86 | 20.04 |
| [$H_2 + CO_2/H_2O + CO$] | 38.97 | 27.31 | 51.81 | 27.94 | 38.18 |

EXAMPLE 4

This example illustrates less effective selectivation when combined with activation. In this example the wet syngas had the composition $H_2/CO=0.6$, with $H_2O/[H_2+CO]=0.1$. The conditions for the concurrent activation-selectivation were the same as for Example 3, except that the treatment time was 6.5 hours instead of 3.8. Thus, the main difference in the two examples was the lower $H_2/CO$ ratio in Example 4.

Subsequent synthesis runs were made as in Example 1B, and the results are summarized in Table IV. Methane and liquid hydrocarbon selectivities are shown in FIG. 4.

EXAMPLE 5

This is a further example of combined activation and selectivation, and the procedure was the same as that in Example 3 except that a wetter syngas was used for 4.5 hours. In particular, in this example the syngas composition was $H_2CO=1.9$, with $H_2O/[H_2+CO]=0.3$.

Figure 5A:
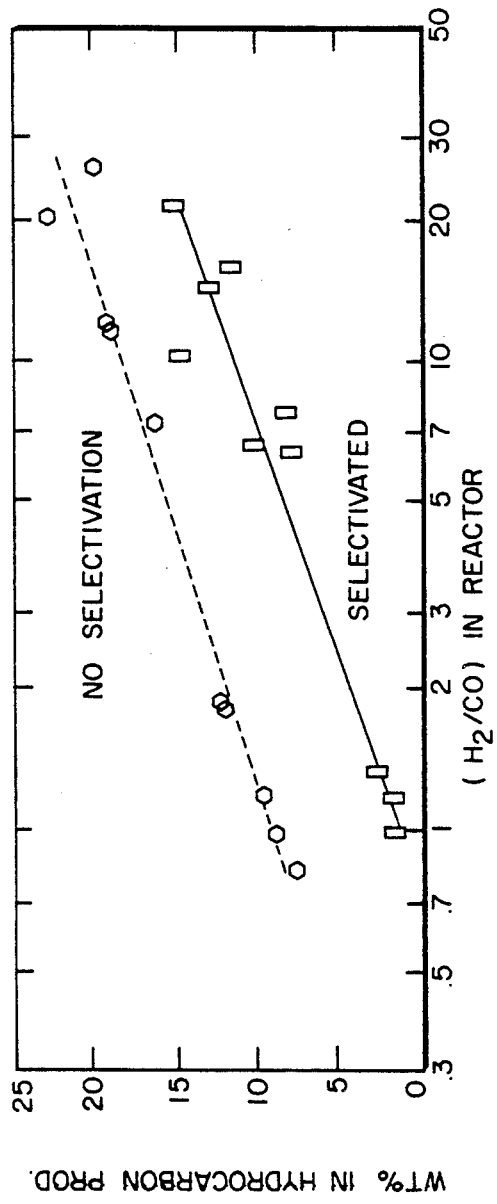
FIGS. 5A and 5B respectively show methane and liquid hydrocarbon ($C_{5+}$) selectivity as a function of feed composition for Example 5.
Figure 5B:
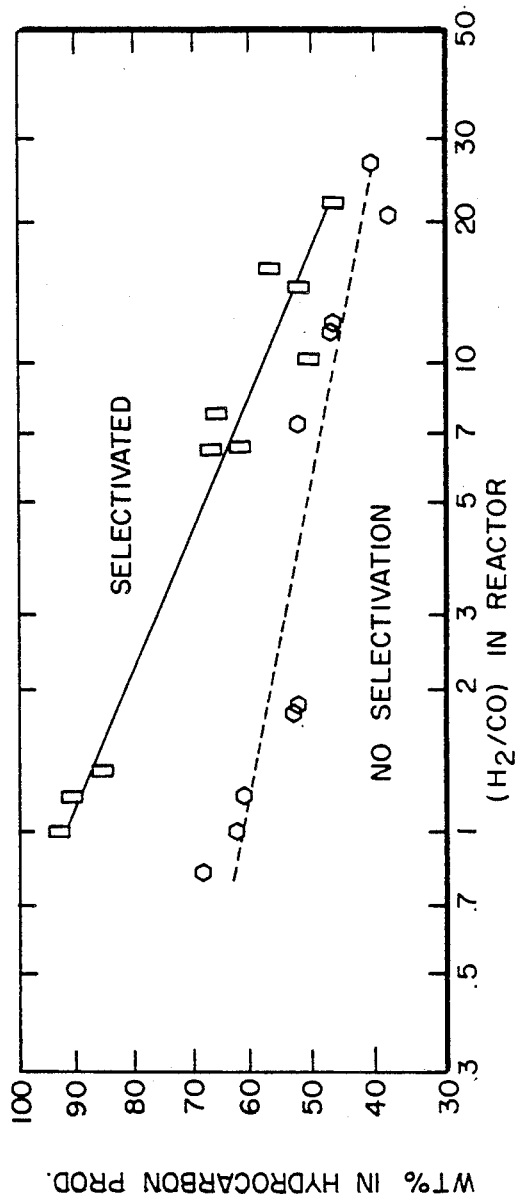

The results of the synthesis runs subsequent to the activation-selectivation treatment are summarized in Table V, and the selectivity for methane and liquid hydrocarbon is shown in FIGS. 5A and 5B, respectively.

TABLE V (EXAMPLE 5)

| | RUN BALANCE | | | | |
|---|---|---|---|---|---|
| | A | B | C | D | E |
| HOURS ON STREAM | 23.33 | 28.08 | 48.00 | 53.08 | 71.08 |
| TEMPERATURE °C. | 265.00 | 266.00 | 265.00 | 265.00 | 266.00 |
| PRESSURE PSIG | 235.00 | 235.00 | 235.00 | 235.00 | 240.00 |

TABLE V-continued
(EXAMPLE 5)

| | | | | | |
|---|---|---|---|---|---|
| SV NL/GFE/HR | 1.26 | 2.42 | 0.67 | 2.42 | 1.28 |
| FEED [$H_2$/CO] | 1.92 | 1.92 | 1.92 | 1.92 | 1.92 |
| SYNGAS CONV % | 56.83 | 54.21 | 70.58 | 54.55 | 63.60 |
| $H_2$ CONV % | 40.23 | 39.55 | 57.26 | 40.20 | 47.95 |
| CO CONV % | 88.78 | 82.41 | 96.22 | 82.15 | 93.72 |
| HYDROCARBON SELECTIVITIES, WT % OF HC | | | | | |
| $CH_4$ | 14.89 | 10.26 | 15.46 | 8.24 | 12.00 |
| $C_2H_6$ | 6.88 | 4.22 | 8.35 | 3.32 | 5.75 |
| $C_2H_4$ | 1.90 | 2.48 | 1.90 | 2.61 | 1.83 |
| $C_3H_8$ | 3.84 | 2.38 | 5.08 | 2.02 | 3.31 |
| $C_3H_6$ | 9.56 | 8.54 | 11.11 | 7.85 | 9.16 |
| $C_4H_{10}$ | 3.13 | 2.35 | 3.84 | 2.05 | 2.82 |
| $C_4H_8$ | 7.63 | 7.17 | 7.10 | 6.57 | 7.37 |
| $C_5+$ | 52.18 | 62.60 | 47.16 | 67.33 | 57.76 |
| EXIT [$H_2$/CO] | 10.25 | 6.61 | 21.74 | 6.45 | 15.96 |
| [$H_2$ + $CO_2$/$H_2O$ + CO] | 27.16 | 15.11 | 40.09 | 14.39 | 30.04 |

| | RUN BALANCE | | | | |
|---|---|---|---|---|---|
| | F | G | H | I | J |
| HOURS ON STREAM | 76.25 | 95.33 | 100.75 | 168.33 | 173.08 |
| TEMPERATURE °C. | 266.00 | 265.00 | 265.00 | 265.00 | 267.00 |
| PRESSURE PSIG | 240.00 | 240.00 | 240.00 | 240.00 | 230.00 |
| SV NL/GFE/HR | 2.52 | 1.32 | 2.46 | 0.72 | 2.46 |
| FEED [$H_2$/CO] | 1.92 | 0.63 | 0.63 | 0.63 | 1.92 |
| SYNGAS CONV % | 55.33 | 84.60 | 78.09 | 88.34 | 64.10 |
| $H_2$ CONV % | 39.85 | 78.50 | 71.97 | 82.85 | 48.97 |
| CO CONV % | 85.11 | 88.45 | 81.95 | 91.81 | 93.23 |
| HYDROCARBON SELECTIVITIES, WT % OF HC | | | | | |
| $CH_4$ | 8.49 | 1.89 | 1.63 | 2.70 | 13.01 |
| $C_2H_6$ | 3.59 | 0.64 | 0.38 | 1.47 | 6.70 |
| $C_2H_4$ | 2.47 | 1.41 | 1.32 | 1.45 | 2.26 |
| $C_3H_8$ | 2.07 | 0.35 | 0.27 | 0.63 | 3.53 |
| $C_3H_6$ | 7.96 | 2.53 | 1.96 | 3.78 | 10.41 |
| $C_4H_{10}$ | 2.03 | 0.38 | 0.27 | 0.69 | 2.74 |
| $C_4H_8$ | 6.63 | 2.20 | 1.53 | 3.40 | 7.68 |
| $C_5+$ | 66.76 | 90.59 | 92.64 | 85.88 | 53.66 |
| EXIT [$H_2$/CO] | 7.77 | 1.18 | 0.98 | 1.32 | 14.50 |
| [$H_2$ + $CO_2$/$H_2O$ + CO] | 17.26 | 22.32 | 19.93 | 25.87 | 29.36 |

DETAILED DESCRIPTION, PREFERRED EMBODIMENTS AND BEST MODE

Preparation of Selectivated Catalyst

For purposes of the present invention, the conventional catalytically inactive iron catalyst must be activated by contact at elevated temperature with reducing gas, and it also must be contacted at elevated temperature with water vapor at sufficiently high partial pressure to induce substantially improved selectivity (selectivation), at least as great as that shown by Example 4, above, and typically larger, as illustrated by Example 5. Although the examples illustrate selectivation and activation of a precipitated iron catalyst, it is contemplated that the improved method of this invention is applicable to other inactive catalyst precursors including fused magnetite and iron oxide impregnated on an inorganic carrier (support) such as kieselguhr. Although it is preferred for purposed of this invention to prepare selectivated activated iron catalyst from freshly prepared inactive catalyst precursor (i.e. "fresh" catalyst), it is contemplated that, in some instances, iron catalyst that has been regenerated by burning in air also may be treated by the method of this invention. In all cases the preparation of the inactive precursor, including steps such as calcination and addition of potassium prior to activation, are conventional and are not considered part of the present invention. It is preferred for purposes of this invention that the inactive precursor contain potassium equivalent to about 0.2 to about 0.6 wt% potassium carbonate. Activation is effected by contact at elevated temperature with gaseous hydrogen, carbon monoxide, or a mixture thereof. It is preferred in this invention to use a flow of syngas for activation, the syngas consisting of hydrogen and carbon monoxide in the ratio of about 0.4 to about 3.0. Such gas is readily available in a Fischer-Tropsch plant.

Selectivation may follow activation, or it may be done concurrently with activation. In either case the inactive iron catalyst may be conveniently prepared for activation and selectivation by grinding the dried catalyst and charging the ground material to a reactor filled with a suitable hydrocarbon liquid medium, as illustrated in the foregoing examples. The reactor is then brought to treatment temperature and pressure while it is vigorously agitated with an inert gas ($N_2$, $CO_2$). (See Koelbel and Ralek, ibid, p. 246.)

When selectivation according to the method of this invention follows activation, the activation step per se is conventional and need not be described here in detail. Such activation is illustrated in Example 1B for a precipitated iron catalyst precursor. Selectivation, illustrated in Example 2, is achieved by treating the active catalyst (in the absence of syngas) with steam, or with steam diluted with an inert gas such as $N_2$ or $CO_2$, at 160° to 350° C. for from 0.5 to about 100 hours. Shown in Table A are conditions effective for selectivation following activation.

TABLE A
SELECTIVATION FOLLOWING ACTIVATION

| | Temp, °C. | Time, hrs. | Partial Pressure $H_2O$, PSI |
|---|---|---|---|
| Broad | 160°–350° | 0.5–100 | 1–500 |
| Preferred | 200°–300° | 1–35 | 5–300 |

TABLE A-continued

SELECTIVATION FOLLOWING ACTIVATION

| | Temp, °C. | Time, hrs. | Partial Pressure H$_2$O, PSI |
|---|---|---|---|
| Particularly Pref'd. | 230°–270° | 3–20 | 10–200 |

As shown by Example 3, selectivation may be conducted during activation. The term "during activation" as used herein means during at least a portion of the time while the catalyst is being activated by syngas, or by hydrogen, or by carbon monoxide. It is preferred to at least initiate activation with flowing, dry syngas, and thereafter to cofeed sufficient water to effect activation. When hydrogen gas is used as the sole reducing gas, the same conditions as shown in Table A (above) are effective to prepare the selectivated activated catalyst of this invention. However, when syngas is used for selectivation during activation, the effective conditions are shown in Table B.

TABLE B

SELECTIVATION DURING ACTIVATION WITH SYNGAS

| | Temp, °C. | Time, Hrs. | Pressure* | FEED COMPOSITION H$_2$O / (H$_2$ + CO + H$_2$O) | H$_2$ / (H$_2$ + CO) |
|---|---|---|---|---|---|
| Broad | 160°–350° | 0.5–100 | 10–200 | 0.05–0.9 | 0–1.0 |
| Pref'd | 200°–300° | 1–35 | 14–80 | 0.08–0.7 | 0.2–0.9 |
| Partic. Pref'd | 230°–270° | 3–20 | 25–60 | 0.1–0.4 | 0.33–0.75 |

*Total Pressure, psig

The best mode contemplated for preparing a stationary bed of selectivated activated catalyst is to first activate the catalyst and then to selectivate it using H$_2$O optionally with inert carrier gas, thereby avoiding problems with temperature control. In a slurry reactor, however, selectivation during activation is likely to be faster and is preferred.

Effective selectivation by the method of this invention produces a readily measurable enhanced steady-state selectivity when compared with a conventional catalyst compared under the same synthesis conditions including syngas feed composition and reaction temperature. The enhanced selectivity is persistent, as illustrated by the above examples. The reason for the enhanced selectivity is not understood, but clearly depends on the treatment with steam. That this effect is not obtained from the steam formed during synthesis (see Equation (I) and (II) above) can be rationalized as probably due to insufficient partial pressure to be effective.

It will be recognized by one skilled in the art that cofeeding syngas and CO$_2$ will form steam according to Equation (II) above, and that CO$_2$ may be effective for selectivation. We have indeed found this to be true, and such method is contemplated as within the scope of this invention as claimed. However, we find that very high pressures of CO$_2$ are required to give an effective selectivation, and this method is distinctly not preferred.

An obvious advantage is derived from the catalyst of this invention by simply substituting it for the similar type conventional iron catalyst used in a Fischer-Tropsch hydrocarbon plant. Reduced methane make with concomitant increase in normally liquid hydrocarbons provides a distinct economic advantage. However, one skilled the art would also recognize that increased selectivity might be traded for increased conversion. Simple calculation based on the catalyst of Example 3, above, for instance, suggests that an increase of operating temperature to allow a fourfold increase of conversion rate is achieved without encountering selectivity poorer than provided by the conventional catalyst of the lower operating temperature. This represents an impressive saving in cost attributable to capital investment. Finally, the improved catalyst provides the plant operator with a new degree of flexibility by permitting adjustment of optional tradeoff as demand for product varies, this adjustment being effected by mere change of operating temperature.

Conversion Process

The improved Fischer-Tropsch conversion process of this invention utilizes as catalyst the selectivated activated iron catalyst described above.

The particular Fischer-Tropsch process that benefits from use of the improved catalyst of this invention is commonly characterized as a "medium pressure" synthesis, and utilizes an iron catalyst. Medium pressure synthesis (with iron catalyst) is conducted at approximately 150 to 450 psig total pressure. Catalyst life is favored by operating at high space velocities. Fixed (static) bed, entrained fluid-bed and slurry reactors may be used, although other variants such as fixed fluid-bed and oil-submerged catalyst have been studied. The fixed-bed and entrained fluid-bed are of commercial importance. The fixed-bed version utilizes precipitated iron catalyst promoted with potassium and copper, and the entrained fluid-bed version a fused magnetite promoted with potassium and other optional promoters including structural promoters such as MgO. Operating temperatures fall into the approximate range of 220° to 350° C., with the fixed-bed process operation being in the range of about 220°–255° C. In the fixed-bed process, a catalyst life of six to twelve months is achieved during which the operating temperature is increased from the starting point of 220° C. to a maximum of 255° C. For further details on the commercial process, see "Carbon Monoxide—Hydrogen Reactions", Ibid, esp. pp. 465–477 and references contained therein. The foregoing description refers to the conventional versions of the Fischer-Tropsch process for synthesizing hydrocarbons with iron catalyst, and is not per se considered part of the present invention.

The conventional synthesis is benefited by treatment of the catalytically inactive iron catalyst precursor, as described above, and by utilizing the resulting selectivated activated catalyst in place of the conventional catalyst. Maintaining the same operating conditions results in improved yield of liquid hydrocarbons with increased yields of oil boiling in the diesel fuel range, and decreased yields of methane, C$_2$ and C$_3$ hydrocarbons. Additionally, with precipitated iron catalyst, higher end-of-run temperatures may be used without encountering uneconomical levels of methane formation. Other process optimizations are permitted by the improved process of this invention, as indicated above.

The preferred variant of the Fischer-Tropsch process for purposes of this invention is that which uses a precipitated iron catalyst that contains potassium promoter in the range equivalent to 0.2 to 0.6 wt% potassium carbonate.

Cross Reference

The Examiner's attention is called to related copending U.S. Patent Application Ser. No. 07/324,795, filed on even date herewith.

What is claimed is:

1. In a method for preparing a catalytically active Fischer Tropsch promoted iron catalyst, which method comprises activating an inactive catalyst precursor comprising an iron oxide and a promoting amount of potassium, said iron oxide being selected from the group consisting of precipitated iron oxide, fused magnetite, and iron oxide impregnated on a carrier, said activation being effected by contact of said inactive catalyst precursor with gaseous hydrogen, carbon monoxide, or a mixture thereof at elevated temperature, the improvement which comprises:
   contacting said catalyst precursor with water vapor during or after said activation step, said contacting with water vapor being conducted under a combination of conditions including a temperature of about 160° C. to about 350° C., a water vapor partial pressure of about 1 (one) to 500 psig, and for about 0.5 to 100 hours, said combination being effective to increase the selectivity of the activated catalyst for forming liquid hydrocarbons whereby forming selectivated activated catalyst.

2. The method described in claim 1 wherein said step of contacting with water vapor is conducted during said activation step.

3. The method described in claim 1 wherein said step of contacting with water vapor is conducted after said activation step.

4. The method described in claim 1 wherein said formed selectivated activated catalyst is virgin catalyst.

5. In a method for preparing fresh catalytically active Fischer Tropsch promoted iron catalyst, which method comprises activating an inactive catalyst precursor comprising a precipitated iron oxide and about 0.2 to about 0.6 wt% potassium carbonate, said activation being effected by contact of said inactive catalyst precursor with a gaseous mixture of hydrogen and carbon monoxide at elevated temperature, the improvement which comprises:
   contacting said catalyst precursor with water vapor during or after said activation step, said contacting with water vapor being conducted under a combination of conditions including a temperature of about 160° C. to about 350° C., a water vapor partial pressure of about 1 (one) to 500 psig, and for about 0.5 to 100 hours, said combination being effective to increase the selectivity of the activated catalyst for forming liquid hydrocarbons whereby forming selectivated activated catalyst.

6. The method described in claim 5 wherein said step of contacting with water vapor is conducted in the presence of said gaseous mixture of hydrogen and carbon monoxide during said activation step.

7. The method described in claim 5 wherein said step of contacting with water vapor is conducted in the absence of said gaseous mixture of hydrogen and carbon monoxide after said activation step.

8. The method described in claim 6 wherein said activation of said inactive catalyst is effected by contact with flowing wet syngas at a temperature of about 200° to about 300° C. for at least about 1 to about 35 hours at a total pressure of about 14 to 80 psig, and at a partial pressure of water vapor sufficient to provide an $H_2O/(H_2+CO+H_2O)$ ratio in the reactor in the range of about 0.08 to 0.7.

9. The method described in claim 7 wherein said contacting with water vapor is effected at about 200° to 300° C. for about one to 35 hours at a water vapor partial pressure of 5 to about 300 psi.

10. The catalyst prepared by the method of claim 1.
11. The catalyst prepared by the method of claim 2.
12. The catalyst prepared by the method of claim 3.
13. The catalyst prepared by the method of claim 4.
14. The catalyst prepared by the method of claim 5.
15. The catalyst prepared by the method of claim 6.
16. The catalyst prepared by the method of claim 7.
17. The catalyst prepared by the method of claim 8.
18. The catalyst prepared by the method of claim 9.

* * * * *